(12) United States Patent
Skinner et al.

(10) Patent No.: US 6,716,595 B2
(45) Date of Patent: *Apr. 6, 2004

(54) METHOD FOR DETECTING SPHINGOSINE-1-PHOSPHATE (S1P) FOR CANCER DETECTION

(75) Inventors: Michael K. Skinner, Pullman, WA (US); Jodi L. Johnson, Beaverton, WA (US); Jeff A. Parrott, Irvine, CA (US)

(73) Assignee: LPL Technologies, Inc., Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/133,012

(22) Filed: Apr. 26, 2002

(65) Prior Publication Data

US 2002/0127628 A1 Sep. 12, 2002

Related U.S. Application Data

(62) Division of application No. 09/661,988, filed on Sep. 14, 2000, now Pat. No. 6,448,023.

(51) Int. Cl.$^7$ .............................. C12Q 1/66; C12Q 1/00; G01N 33/53
(52) U.S. Cl. ................................ 435/8; 435/4; 435/968
(58) Field of Search .................................. 435/8, 4, 968

(56) References Cited

U.S. PATENT DOCUMENTS

| | | | | |
|---|---|---|---|---|
| 5,376,531 A | * | 12/1994 | Anderson et al. | 435/7.23 |
| 5,430,169 A | | 7/1995 | Boumendjel et al. | 558/169 |
| 5,583,160 A | | 12/1996 | Igarashi et al. | 514/669 |
| 5,627,171 A | | 5/1997 | Park et al. | 514/114 |
| 5,677,189 A | * | 10/1997 | Igarashi et al. | 436/57 |

FOREIGN PATENT DOCUMENTS

WO    WO 99/41266    8/1999

OTHER PUBLICATIONS

Byers, David et al., *Vibrio harveyi* Aldehyde Dehydrogensase, Partial Reversal of Aldehyde Oxidation and Its Possible Role in the Reduction of Fatty Acids for the Bioluminescence Reaction, J. of Biol. Chem., vol. 259, No. 11, Jun. 10 pp. 7109–7114, 1984.

Byers, David et al., "Differential Regulation of Enzyme Activities Involved in Aldehyde Metabolism in the Luminescent Bacterium *Vibrio harveyi*," J. of Bacteriology, Feb. 1988 p. 967–971.

Byers, David, "Elongation of Exogenous Fatty Acids by the Bioluminescent Bacterium *Vibrio harveyi*," J. of Bacteriology, Jan. 1989, p. 59–64.

Carey, Luc M., et al. "Generation of Fatty Acids by an Acyl Esterase in the Bioluminescent System of *Photobacterium phosphoreum*," J. of Biol. Chem., vol. 259, No. 16 Aug. 25 pp. 10216–10221, 1984.

Day, John I.E., et al. "Enzymatic reduction of long–chain acyl–CoA to fatty aldehyde and alcohol by extracts of *Clostridium butyricum*," Biochem. Biophys, Acts, 218 (1970) 179–182.

Dunn, D.K., et al. "Conversion of Aldehyde to Acid in the Bacterial Bioluminescent Reaction," Biochemistry, vol. 12 No. 24 p. 4911–4918, 1973.

Eberhard, Anatol et al. "Quantitative Analysis of the Phospholipids of Some Marine Bioluminescent Bacteria," Lipids vol. 6. No. 6. pp. 410–414, 1971.

Goetzl, Edward J. et al., "Diversity of cellular receptors and functions of the lysophospholipid growth factors lysophosphatidic acid and sphingosine 1–phosphate," The FASEB Journal, vol. 12, Dec. 1998, pp. 1589–1598.

Gonda, Koichi, et al. "The novel sphingosine 1–phosphate receptor AGR16 is coupled via pertussis toxin–sensitive and –insensitive G–proteins to multiple signalling pathways," Biochem. J. (1999) 67–75.

Jablonski, Edward, et al. "Studies of the Control of Luminescence in *Beneckea harveyi*: Properties of the NADH and NADPH:FMN Oxidoreductases," Biochemistry, vol. 17 No. 4 1978 pp. 672–678.

James, Paul F., et al. "Isolation of Animal Cell Mutants Defective in Long–chain Fatty Aldehyde Dehydrogenase," J. of Biol. Chem., vol. 272, Sep. 19 pp. 23532–23539, 1997.

Jebens, E., et al. "Enzymatic microdetermination of plasma and serum free fatty acids," Scand. J. Clin. Lab. Invest. 1992; 52: 717–724.

Kawaguchi, Akihiko, et al. "An Enzymic Cycling Method for the Determination of Free Fatty Acids with Acyl–CoA Synthetase and Acyl–CoA Hydrolase," J. Biochem. 94, 487–492 (1983).

Kon, Junko, et al. "Comparison of Intrinsic Activities of the Putative Sphingosine 1–Phosphate Receptor Subtypes to Regulate Several Signaling Pathways in Their cDNA–transfected Chinese Hamster Ovary Cells," J. of Biol. Chem., 274: pp. 23940–23947, Aug. 20, 1999.

Kricka, Larry J., et al. "Automated Bioluminescent Assays for NADH, Glucose 6–Phosphate, Primary Bile Acids, and ATP," Analytical Biochemistry, 129, 392–397 (1983).

Kurita, Toyohisa, et al. "Enhancement of hydrolytic activity of sphingolipid ceramide N–deacylase in the aqueous–organic biphasic system," J. of Lipid Research, 41: pp. 846–851, 2000.

Lavi, Jukka, et al. "The Effect of Luciferase and NADH:FMN Oxidoreductase Concentrations on the Light Kinetics of Bacterial Bioluminescence," Biochem. And Biophys. Research Communications, 111: pp. 266–273, Feb. 28, 1983.

Lee, Menq–Jer, et al. "Sphingosine–1–Phosphate as a Ligand for the G Protein–Coupled Receptor EDG–1,": Science, 279: 1552–1555, Mar. 6, 1998.

(List continued on next page.)

Primary Examiner—Louise N. Leary
(74) Attorney, Agent, or Firm—Baker & Hostetler LLP

(57) ABSTRACT

The present invention relates to non-radioactive enzymatic methods for detecting Sphingosine-1-Phosphate (S1P) in biological fluids. The present invention further relates to a method of detecting the presence of cancer in a patient by the use of these and other methods of detecting S1P in biological samples from a patient.

27 Claims, No Drawings

OTHER PUBLICATIONS

Okamoto, Hiroyuki, et al. "EDG1 Is a Functional Sphingosine-1-Phosphate Receptor That is Linked via a $G_{i/o}$ to Multiple Signaling Pathways, Including Phospholipase C Activation, $Ca^{2+}$ Mobilization, Ras–Mitogen–Activated Protein Kinase Activation, and Adenylate Cyclase Inhibition," J. of Biol. Chem., 273: pp. 27104–27110, Oct. 16, 1998.

Reindeau, Denis, et al. "Evidence for a Fatty Acid Reductase Catalyzing the Synthesis of Aldehydes for the Bacterial Bioluminescent Reaction," J. of Biol. Chem. 254: pp. 7488–7490 Aug. 25, 1979.

Reindeau, Denis, et al. "Co–induction of Fatty Acid Reductase and Luciferase during Development of Bacterial Bioluminescence," J. of Biol. Chem. 255: pp. 12060–12065 Dec. 25, 1980.

Reindeau, Denis, et al. "Enzymatic reduction of fatty acids and acyl–CoAs to long chain aldehydes and alcohols," Experientia 41: (1985) pp. 707–713.

Rodriguez, Angel, et al. "Purification of the Acyl Coenzyme A Reductase Component from a Complex Responsible for the Reduction of Fatty Acids in Bioluminescent Bacteria," J. of Biol. Chem., 258: pp. 5233–5237, Apr. 25, 1983.

Rodriguez, Angel, et al. "Fatty Acyl–AMP as an intermediate in Fatty Acid Reduction to Aldehyde in Luminescent Bacteria," J. of Biol. Chem., 260: pp. 771–774, Jan. 25, 1985.

Saba, Julie D., et al. "The BST1 Gene of *Saccharomyces cerevisiae* is the Sphingosine–1–Phosphate Lyase," J. of Biol. Chem., 272: pp. 26087–26090, Oct. 17, 1997.

Sato, Koichi, et al. Downregulation of mRNA Expression of Edg–3, a Putative Sphingosine 1–Phosphate Receptor Coupled to $Ca^{2+}$ Signaling, during Differentiation of HL–60 Leukemia Cells, Biochem. and Biophys. Research, Communications, 253: pp. 253–256, 1998.

Sato, Koichi, et al. Possible Involvement of Cell Surface Receptors in Sphingosine 1–Phosphate Induced Activation of Extracellular Signal–Regulated Kinase in C6 Glioma Cells, Molecular Pharmacology, 55: 126–133 (1999).

Styrélius, Anders Thore, et al. "Bioluminescent Assay for Total Bile Acids in Serum with Use of Bacterial Luciferase," Clinical Chemistry, 29: pp. 1123–1127, 1983.

Ugarova, N.N., et al. "Bioluminescent Microassay of Various Metabolites Using Bacterial Luciferase Co–immobilized with Multienzyme Systems," Analytical Biochemistry 173: pp. 221–227 (1988).

Van Veldhoven, Paul P., et al. "Subcellular Localization and Membrane Topology of Sphingosine–1–Phosphate Lyase in Rat Liver," J. of Biol. Chem., 266: pp. 12502–12507, 1991.

Van Veldhoven, Paul P., et al. "Sphingosine–Phosphate Lyase," Advances in Lipid Research, 26: pp. 69–98, 1993.

Van Veldhove, Paul P., et al. "On the presence of phosphorylated sphingoid bases in rat tissues A mass–spectrometric approach," FEBS Letters 350: pp. 91–95, 1994.

Van Veldhove, Paul P., et al. "Sphingosine–1–Phosphate Lyase," Methods in Enzymology, 311: pp. 244–254 1999.

Wall, Lee A., et al. "In Vivo and In Vitro Acylation of Polypeptides in *Vibrio harveyi*: Identification of Proteins Involved in Aldehyde Production for Bioluminescence," J. of Bacteriology, 159: pp. 720–724, Aug. 1984.

Van Veldhoven, Paul P., et al. "Sphingosine 1–Phosphate Regulates Melanoma Cell Botility through a Receptor–Coupled Extracellular Action and in a Pertussis Toxin–Insensitive Manner," Biochemistry 1997, 36: pp. 10751–10759.

* cited by examiner

METHOD FOR DETECTING SPHINGOSINE-1-PHOSPHATE (S1P) FOR CANCER DETECTION

RELATED APPLICATIONS

This application is a divisional of U.S. application Ser. No. 09/661,988 filed on Sep. 14, 2000 now U.S. Pat. No. 6,448,023, allowed. The priority of the prior application is expressly claimed, and the disclosure of each of these prior applications is hereby incorporated by reference in its entirety.

FIELD OF THE INVENTION

The present invention relates to non-radioactive enzymatic methods for detecting Sphingosine-1-Phosphate (S1P) in biological fluids and the correlation at a measurement of S1P to disease. The present invention further relates to a method of detecting the presence of cancer in a patient by the use of these and other methods of detecting S1P in biological samples from a patient.

BACKGROUND OF THE INVENTION

Sphingolipids are a diverse group of molecules that are found in the membranes of all eukaryotic cells (Merrill et al., *Toxicol. Appl. Pharmacol.* 142:208–225 (1997)). There are three classes of sphingolipids: sphingomyelins, cerebrosides and gangliosides. Sphingolipids include sphingomyelin, sphinganine, sphingosine, glycosphingolipids and ceramide. Sphingosine-1-phosphate (S1P) is a lysosphingolipid that is generated by the metabolism of sphingomyelin. (Spiegel and Merrill, *FASEB J.* 10:1388–1397 (1996)). Sphingomyelin, the most abundant type of sphingolipid is first converted to ceramide (sphingosine+palmitate residues) by the removal of the head group. Ceramide is then cleaved to form sphingosine by the action of ceramidases. S1P is then generated from sphingosine by the action of sphingosine kinase. S1P may then be further metabolized into ethanolamine-phosphate and long-chain aldehyde (e.g. hexadecanal) by S1P lyase (Zhou and Saba, *Biochemical and Biophysical Research Communications,* 242:502–507 (1998)). The web of enzymatic events governing the metabolism of Sphingolipids is diagrammed below:

In addition to their role as components of biological membranes, some of the metabolites of sphingolipids, such as ceramide, sphingosine and S1P, are potent chemical messengers (Spiegel and Merrill, supra, Meyer et al., *FEBS Lett.* 410:34–38 (1997); and Gomez-Munoz et al., *J. Biol. Chem.* 270:26318–26325 (1995)). S1P has been shown to act as an intracellular second messenger that is generated in cells that have been activated by various mitogens (Spiegel et al., *Breast Cancer Res. Treat.* 31:337–348 (1994); Sadahira et al., *Proc. Natl. Acad. Sci. USA* 89:9686–9690 (1992); and Spiegel et al., *Ann. N.Y. Acad. Sci.* 845:11–18 (1998)), and to act as an extracellular ligand for a group of cell surface receptors (Hecht et al., *J. Cell. Biol.* 135:1071–1083 (1996); An et al., *Biochem. Biophys. Res. Commun.* 231:619–622 (1997); Goetzl and An, *FASEB J.* 12:1589–1598 (1998); van Koppen et al., *J. Biol. Chem.* 274:18997–19002 (1999); Yatomi et al., *J. Biol. Chem.* 272:5291–5297 (1997); and Ancellin and Hla, *J. Biol. Chem.* 274:18997–19002 (1999)). S1P is the principal ligand for three G-protein coupled receptors known as endothelial cell differentiation gene-1, -3 and -5 (Edg-1, Edg-3 and Edg-5). Edg-1, -3 and -5 are expressed in a variety of human tissues. Edg-1 is ubiquitously expressed (Goetzl and An, supra). Edg-3 is abundant in cardiovascular tissue and leukocytes, and is also expressed widely (Id.). Edg-5 is found most abundantly in cardiovascular tissue, the central nervous system, gonadal tissue and the placenta (Id.). The presence of multiple, high affinity receptors for S1P and their wide distribution, may provide redundancy in the control of the biological processes mediated by S1P. Another possibility is that specific S1P-directed biological processes are achieved by differential coupling between the various receptors and G-proteins (Ancellin and Hla, supra). However, the full role of S1P in normal and abnormal cell function has not yet been elucidated.

Previously, S1P levels have been measured quantitatively in biological samples by various methods utilizing the addition of radioactive isotopic moieties to the molecule. One such method is the determination of the amount of radioactive acetic anhydride that is incorporated in S1P by acylation (Yatomi et al., *Anal. Biochem.* 230:315–320 (1995)). In this assay, the S1P is first extracted from cells

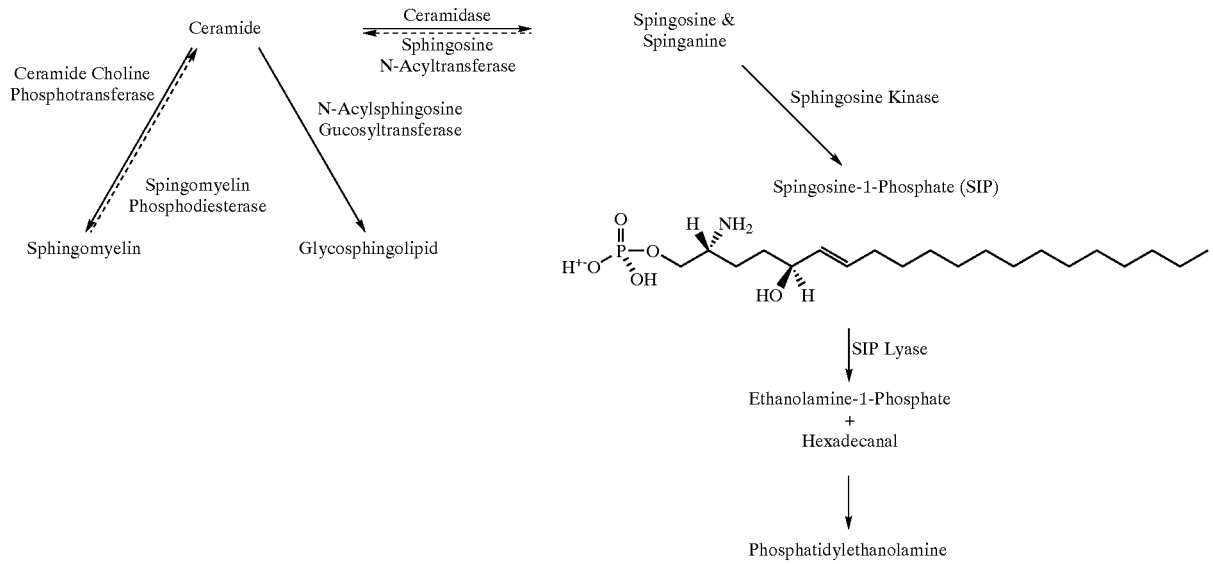

into an upper aqueous phase under alkaline conditions, and then re-extracted into the lower chloroform phase under acidic conditions. The phosphorylated sphingoid base is then quantitatively converted to N-[$^3$H]-acetylated S1P by N-acylation with [$^3$H] acetic anhydride, forming C2-Cer-1-P (tritiated C2-ceramide 1-phosphate). The C2-Cer-1-P is resolved with thin-layer chromatography, detected with autoradiography, and quantified with a scintillation counter. The assay permits quantification of S1P over a range of at least 100 pmol to 10 nmol. Yatomi used this assay to measure the distribution of S1P in various organs in rats. The largest concentration of S1P was in the testis and intestine (~100 nmol S1P/gram of tissue), followed by the spleen and brain (~50 nmol S1P/gram of tissue) (Yatomi et al., *FEBS Lett.* 404:173–174 (1997)). The kidney, heart and lung contained between 10 and 20 nmol S1P/gram of tissue, with the liver and muscle containing the lowest concentration of S1P (<5 nmol S1P/gram of tissue).

Using their assay, Yatomi and coworkers measured the level of S1P in some human bodily fluids (Yatomi et al., *J. Biochem.* (*Tokyo*) 121:969–973 (1997)). They determined the concentration of S1P in normal human plasma and serum, but were unable to detect S1P using their assay in urine, ascites, pleural effusion or cerebrospinal fluid. They determined that tritiated sphingosine was rapidly taken into platelets in platelet-rich serum, while S1P was stable, demonstrating that the enzymes required for S1P degradation are not present in serum (Yatomi et al., *J. Biochem.* (*Tokyo*), supra). The authors suggested that the release of S1P from activated platelets might be involved in processes such as thrombosis, hemostasis, atherosclerosis and wound healing.

S1P has also been detected using an enzymatic method employing an alkaline lipid extraction to separate S1P from other phospholipids and sphingolipids (Edsall and Spiegel, *Anal. Biochem.* 272:80–86 (1999)). The extracted S1P was converted to sphingosine by alkaline phosphatase treatment. The sphingosine was then quantitatively phosphorylated using recombinant sphingosine kinase and [$\gamma^{32}$P]ATP. The authors reported that levels of S1P varied in rat tissues between 0.5 and 6 pmol/mg wet wt. The lowest levels were found in heart and testes, while the brain contained the highest levels.

These prior known methods for measuring S1P focus on the incorporation of a radioactive isotopic moiety into the molecule, and require considerable processing time in the laboratory. These limitations make the current assays unsuitable for many clinical or laboratory settings where complex bench processes are not practical. Development of a rapid and sensitive non-radioactive assay for S1P would facilitate use of this compound as a marker for various cellular activities such as cell growth, cell migration, apoptosis, platelet activation, changes in cellular morphology and for detecting conditions associated with altered levels of S1P.

Cancers such as ovarian cancer, lung cancer, colon cancer, and breast cancer are among the most frequent causes of cancer death in the United States and Europe. Despite decades of cancer research, mortality rates among persons who contract cancer remain high. However, when a cancer is detected at an early stage, survivability increases dramatically. For example, when ovarian cancer is diagnosed at an early stage, the cure rate approaches 90%. In contrast, the 5 year outlook for women with advanced disease remains poor with no more than a 15% survival rate. Thus, early diagnosis is one of the most effective means of improving the prognosis for cancer.

Frequently, however, detection of cancer depends upon the detection and inspection of a tumor mass which has reached sufficient size to be detected by physical examination. The detection of molecular markers of carcinogenesis and tumor growth can solve many of the problems which the physical examination of tumors have encountered. Samples taken from the patient for screening by molecular techniques are typically blood or urine, and thus require minimally invasive techniques. Thus, they can be used on a regular basis to screen for cancers. In addition, because molecular markers often appear before the tumor is of a detectable size, it is possible to detect cancers at very early stages in the progression of the disease.

SUMMARY OF THE INVENTION

The present invention provides a molecular marker for screening and diagnosis of disease while overcoming the deficiencies in the current methods of measuring S1P by providing simple enzymatic methods for determining concentrations of S1P in samples of biological fluids such as serum or plasma. The methods utilize the enzymatic cleavage of S1P by to produce ethanolamine-phosphate and long-chain aldehyde (e.g. hexadecanal), and a separate second enzymatic step which produces a detectable signal that can be used to calculate the concentration of S1P in the sample.

In the various embodiments of this aspect of the invention, the concentration of S1P is detected in a sample of bodily fluid taken from a patient. The S1P in the sample is preferably first enriched through extraction of sphingolipids. S1P in the sample is digested in the first enzymatic step with S1P lyase, to generate long-chain aldehyde (e.g. hexadecanal) and ethanolamine-phosphate. In the second step of the enzymatic detection aspect, either S1P or one of the products of the enzymatic cleavage is utilized as a substrate by an enzyme that produces a product which can be detected by chemiluminescent, fluorescent, spectraphotometric or colorimetric methods the second step. In more preferred embodiments of the invention, an oxidation-reduction reaction is utilized in the second step to produce a detectable signal via enzymes that amplify the signal which is detected by chemiluminescent, fluorescent, spectraphotometric or colorimetric methods the second step. In preferred embodiments of the invention, a portion of the sample extract which is not subjected to the first enzymatic step is subjected to the second enzymatic step as a control to accurately measure the increase or decrease in the signal caused by the digestion of S1P by S1P lyase in the first enzymatic step.

Another embodiment of the S1P detection methods of the present invention is a diagnostic kit containing enzymes and other reagents for conducting the enzymatic assays of the invention to measure the concentration of S1P in samples of bodily fluids taken from patients.

In another aspect of the present invention, altered levels of S1P in a sample of bodily fluid taken from a human patient, as compared to normal levels of S1P, are used to detect cancer in the patient. The enzymatic methods of the invention, as well as other methods of measuring S1P, may be utilized in this aspect of the invention. The determination of abnormal S1P concentration may be made by comparison with a numerical or experimental standard or by determining a change in the S1P level of a patient over time. The method of the present invention can be used to detect a broad range of cancers at an early stage. Gynecological cancers, including breast cancer, ovarian cancer, cervical cancer, uterine cancer, endometrial cancer, peritoneal cancer, and fallopian tube cancer, are particularly suitable for detection using the methods of the present invention.

In alternative embodiments of the cancer detection method of the present invention, the concentration of additional markers for cancer in the sample of bodily fluid are also determined, either sequentially or simultaneously. By testing for additional cancer markers, the clinician can increase the accuracy and specificity of a diagnosis based upon the an abnormal level of S1P in the patient's sample. Also, by conducting repeat measurements over time, the clinician can monitor the progression of disease or response to therapy by correlating the change in S1P levels over time to previous values or controls.

DETAILED DESCRIPTION OF THE INVENTION

In the enzymatic detection methods of the invention a bodily fluid sample such as whole blood is collected from a patient. The patient may be any eukaryotic organism, preferably a vertebrate, including, but not limited to, a mammal, a bird, a fish, an amphibian, or a reptile. Preferably, the patient is a mammal, most preferably a human. Bodily fluids include, but are not limited to, plasma, serum, urine, saliva, ascites, cerebral spinal fluid or pleural fluid. As mentioned above, the enzymes necessary to specifically degrade S1P are not found in whole blood. Such stability may facilitate the measurement of S1P in blood products. Thus, whole blood derivatives such as serum or plasma are preferred for the use in the present invention to monitor S1P levels in a patient. However, the methods of the present invention may also be utilized to measure S1P levels in other biological samples if care is taken to minimize degradation of the analyte. General enzymatic inhibitors known in the art, such as E-64 (trans-Epoxysuccinyl-L-leucylamido-(4-guanidino) butane, Sigma); leupeptin (Sigma); pepstatin A (Sigma); TPCK (N-tosyl-L-phenylalanine chloromethyl ketone, Sigma); PMSF (Phenylmethanesulfonyl fluoride, Sigma); benzamidine (Sigma) and 1,10-phenanthroline (Sigma), EDTA (Ethylenediaminetetracetic acid, Sigma) and EGTA (Ethylene glycol-bis-(beta-aminoethyl ether), Sigma) may be used in the collection of such samples. EDTA may also activate the S1P lyase enzyme in the enzymatic detection method.

In order to increase the amount of S1P in the sample, sphingolipids are preferably extracted from the sample. For example, organic extraction using chloroform:methanol and centrifugation can be used to enrich for S1P, as described in Example 1. This organic extraction may be altered by one skilled in the art to optimize for S1P extraction (e.g. acidic or basic conditions). In the methods of the invention, an alternative to the liquid organic extraction for enrichment includes the use of solid phase extraction using, e.g. a Bond-Elut[7] column (Varian, Harbor City, Calif.) consisting of silica or fluorosil can be used to enrich for S1P and to remove proteins and other lipids.

In the preferred embodiments of the invention, S1P is hydrolyzed by S1P Lyase, (Zhou and Saba, supra) into a mixture of ethanolamine-phosphate and long-chain aldehyde (e.g. hexadecanal) in the first enzymatic step. This substrate-specific enzymatic reaction allows for the detection of S1P in the second enzymatic step by either the disappearance of S1P as a substrate for a non-substrate-specific enzymatic reaction, or the appearance of ethanolamine-phosphate or long-chain aldehyde (e.g. hexadecanal) as a substrate for a specific or non-specific enzyme reaction (such as the utilization of long-chain aldehyde, e.g. hexadecanal, by bacterial luciferase in a chemiluminescent reaction.) Although it is preferred that S1P, ethanolamine-phosphate, or long-chain aldehyde (e.g. hexadecanal) be utilized as a substrate by an enzyme which produced a product which may directly be detected by chemiluminescent, fluorescent, or spectraphotometric means, embodiments where the first product produced is an intermediate product/substrate for later enzymatic reactions which produce a detectable product are also envisioned within the present invention. The second enzymatic step preferably comprises additional enzymes to recycle substrates in order to magnify the signal obtained from the utilization of S1P, ethanolamine, or long-chain aldehyde (e.g. hexadecanal) as a substrate.

In preferred embodiments of the invention, the second enzymatic step comprises a luminescent reaction to detect the amount of long-chain aldehyde (e.g. hexadecanal) produced by generating a light signal, which is then detected, for example, using a luminometer. This luminescent reaction utilizes two enzymes, NAD(P)H:FMN oxidoreductase and luciferase, to produce light signal (Ugarova et al., *Anal. Biochem.* 173:221–227 (1988); Dunn, et al., *Biochemistry* 12(24): 4911–4918 (1973); Lavi, et al., *Biochemical and Biophysical Resrch. Communications,* 111(1): 266–273 (1983)). These enzymes catalyze the following reactions:

$$NAD(P)H + FMN + H^+ \rightarrow FMNH_2 + NAD(P)^+ \quad (1)$$

$$FMNH_2 + O_2 + RCHO \rightarrow FMN + RCOOH + H_2O + h\nu \quad (2)$$

(1) NAD(P)H:FMN oxidoreductase reaction
(2) Luciferase reaction

All of the components of the above enzymatic method are added except for long-chain aldehyde (RCHO) which is supplied by the S1P lyase reaction with S1P in the first step. The level of S1P detected is quantified by detecting the luminescence (counts/second) measured by a luminometer (Wallac Victor2 Multilabel Counter, EG&G Wallac, Inc., Gaithersburg, Md.). The difference between the amount of light produced by the luciferase reaction without the addition of S1P lyase in the first enzymatic step of the assay and the amount produced with the addition of S1P lyase is directly proportional to the amount of S1P present. Numerical values are obtained from a standard curve consisting of known amounts of long-chain aldehyde (e.g. hexadecanal from 0 to 100 μM), or by subjecting known amounts of S1P to the first and second enzymatic steps. Assays are preferably performed in duplicate with both positive and negative controls. Background signals in plasma without S1P Lyase are subtracted from all samples. Standard curve values are plotted and fitted to a point-to-point, linear or second-order polynomial curve fit. The levels of S1P in each sample are determined by comparing each signal measured to the standard curve.

In another embodiment, the second enzymatic step utilizes an aldehyde dehydrogenase reaction in the presence of NAD+ to produce a long-chain acid and NADH:

$$RCHO + NAD(P)^+ + H_2O \rightarrow RCOOH + NAD(P)H \quad (1)$$

(1) aldehyde dehydrogenase reaction
The level of S1P detected is quantified by detecting the production of NAD(P)H using UV spectrometry at OD340, colorimetry, fluorescence, or luminescence by standard procedures known in the art. For this reaction, several types of aldehyde dehydrogenase enzymes may be sufficient including NAD-dependent (EC 1.2.1.3) and NAD(P)-dependent (EC 1.2.1.4) enzymes. These enzymes generally interact with short-chain aldehydes. S1P molecules generally contain long-chain sphingosine, and therefore, would result in long-chain aldehydes after S1P lyase treatment. If necessary, a long-chain aldehyde dehydrogenase (EC 1.2.1.48) may be used in this reaction. Use of long-chain aldehyde dehydrogenase may reduce background signal from non-specific short-chain aldehydes and be useful for enzymatic determinations of S1P in unextracted plasma or serum.

In another embodiment, the second enzymatic step utilizes a cycling reaction to amplify the long-chain aldehyde (e.g. hexadecanal) signal. In this cycling reaction, two types of aldehyde dehydrogenase enzymes are used. Aldehyde dehydrogenase enzymes that specifically require NADH or NADPH as cofactors are combined to cycle between long-chain aldehydes and long-chain fatty acids. For example, NAD-dependent aldehyde dehydrogenase and NAD⁻ are utilized to catalyze long-chain aldehyde to long-chain fatty acid. NADP-dependent aldehyde dehydrogenase and NADPH are utilized to catalyze long-chain fatty acid to long-chain aldehyde.

(cycling)

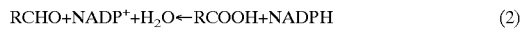

(1) NAD-dependent aldehyde dehydrogenase reaction (2) NADP-dependent aldehyde dehydrogenase reaction Sufficient amounts of NAD- and NADPH are added to this cycling reaction to drive the (1) reaction to the right and the (2) reaction to the left as shown. These reactions are allowed to cycle until sufficient signal is generated. The level of S1P detected is quantified by detecting the production of NADH or the disappearance of NADPH using detection systems specific for NADH or NADPH. One such detection system utilizes a similar luminescent reaction described above. In this reaction, FMN:NAD(P)H oxidoreductases specific for either NADH or NADPH (Jablonski and DeLuca, Biochemistry, 17(4): 672–678 (1978)) are used with luciferase to generate light. This reaction is similar to the bacterial luciferase luminescent reaction described above, however the NADH accumulated or NAD(P)H oxidized from the above cycling reaction is measured instead of the hexadecanal produced by S1P lyase cleavage. For this detection reaction, no additional NADH is added and an excess of long-chain aldehyde reagent is added after the above enzymatic cycling reaction is complete. As a result, the luminescent reaction determines the NADH concentration accumulated in the above enzymatic cycling reaction, which will be proportional to the original concentration of hexadecanal produced in the S1P lyase cleavage reaction.

The above two examples of second enzymatic step detection reactions merely illustrate the principle of the invention. One of ordinary skill in the art would similarly be able to utilize any number of known reactions for the measurement of aldehyde in the sample in order to detect the appearance of long-chain aldehyde (e.g. hexadecanal). Alternatively, other reactions could be utilized to detect the disappearance of a reactive group on S1P or the appearance of a reactive group on ethanolamine-1-phoshate. Thus, by utilizing the substrate-specific S1P lyase reaction, the quantification of S1P in the sample can be achieved by monitoring the subtractive or additive difference in the signal produced by the non-substrate specific second enzymatic step. Because an the detection methods utilize enzymatic reactions to produce a detectable signal, they may be carried out in a reasonable amount of time for use in clinical screening and large-sample-number research settings.

An important advantage of the enzymatic assay of the invention is that the assay may be performed in a microtiter plate format to permit small volumes of samples and reagents to be employed. In addition, the results of the assay may be monitored with automated equipment, e.g. using an ELISA reader. These formats facilitate automating the performance of the assay. Reduced processing times and automated handling using such formats for the assays may reduce variability between results.

The methods of the invention provide a rapid and accurate assay with increased sensitivity for detecting small amounts of S1P present in samples of bodily fluids from patients. The enzymatic assay can be used to detect conditions associated with altered levels of S1P in a sample from a patient as compared to normal samples. The methods of the invention and test kits thus provide a practical means for clinical detection of conditions associated with altered levels of S1P and the monitoring of S1P levels in patients, such as neurodegenerative diseases or the novel detection of cancer described below. In addition, the enzymatic assay of the invention is an important research tool for the exploration of the role of S1P in normal biology and various pathologies.

The enzymatic methods described herein for measuring concentrations of S1P in samples of bodily fluids from a patient may also be performed, for example, by using pre-packaged diagnostic kits. Such kits optionally include components such as enzyme S1P lyase, enzyme reagents for carrying out the second step of the methods of the invention, (e.g. bacterial luciferase, NAD(P)H:FMN oxidoreductase, NADH or NAD(P)H specific aldehyde dehydrogenases, etc.). Also optionally included are ancillary agents such as buffering agents, substrate reagents such as NADH or NAD(P)H, and agents such as EDTA to inhibit subsequent production or hydrolysis of S1P during transport or storage of the samples. Kits embodying the enzymatic method aspect of the invention may also include control standards such as long-chain aldehyde (e.g. hexadecanal), S1P, or ethanolamine-phosphate in defined concentrations. The kits may also include an apparatus or container for conducting the methods of the invention and/or transferring samples to a diagnostic laboratory for processing, as well as suitable instructions for carrying out the methods of the invention. If the kit is to be used in the cancer detection method of the invention, the kit may also optionally include components for the detection of other cancer markers as described below.

Detection of Cancer in Patients by Detection of Abnormal Levels of S1P

The methods of the invention can be used to provide a rapid and economical screen of large numbers of patients to promote early diagnosis of cancer associated with altered levels of S1P. Early detection provided by such methods can significantly improve quality of life and better patient survival rates by permitting the early and aggressive management of the disease at its nascent stages.

In preferred methods of the cancer detection aspect of the invention, the S1P level of the patient is determined or monitored utilizing the enzymatic detection aspect of the invention described above. However, it is also envisioned that alternative methods of measuring S1P in a bodily fluid sample obtained from the patient may be employed in the cancer detection aspect of the invention. For instance, S1P in the biological sample may be measures by fractionating the sample using HPLC or gas chromatographic techniques, or purification/extraction procedures, and then quantified on a mass-spectrometer or by spectraphotometry. Alternatively, antibodies reactive with S1P may be generated using standard methods, for example by immunizing a suitable animal with S1P and an adjuvant to produce antibodies and the fusion and immortalization of spleen cells (prepared as described by Kohler and Milstein (*Nature* 256:495–497)), or by recombinant methods, as are generally known. These monoclonal or polyclonal antibodies may then be used in an assay such as a radio-immunoassay (RIA), enzyme linked immunoassay (ELISA), or other immunoassay formats to detect the presence of S1P in a sample of bodily fluid.

The specific correlation of the level of S1P in the sample with the cancer state is usually specific for the type of sample and type of cancer. For instance, in a plasma sample the level of S1P may be greater than in a serum sample for the same patient with the same cancer condition. In addition, one type of cancer may show a decrease in S1P concentration as compared to normal levels, while another cancer type may show an increase in S1P concentration. Likewise, the use of different extraction procedures to enrich the amount of S1P in the sample will alter the absolute value of the diagnostic threshold. The person of ordinary skill in the art would be capable of determining the proper level of S1P in the sample which is indicative of a particular disease state, given the guidance supplied by this specification and the examples below, utilizing routine experimentation. For instance, one of ordinary skill in the art would know to first establish an positive indicator threshold level of S1P for a particular sample technique (serum, plasma, or urine) by first comparing samples taken from normal patients with those diagnosed as having the particular cancer (breast cancer, ovarian cancer, cervical cancer, uterine cancer, endometrial cancer, peritoneal cancer, and fallopian tube cancer.) Alternatively, normal or control values may be obtained, when known, from published literature. By making a comparison between normal or control values and those indicative of disease, utilizing samples available from various specimen banks and the assay techniques detailed below, one may establish the proper indicative threshold to diagnose a patient as having a particular type of cancer. In general, a finding that a patient has a level of S1P in his or her biological fluids, which deviates significantly from the normal range is a strong indication that the patient has cancer.

In addition to its use as a detection method, the response of a cancer condition to treatment may be monitored by determining concentration of S1P in samples taken from a patient over time. The concentration of S1P is measured and compared to the concentration taken at the earlier time from that patient. If there is a significant change in the concentration of S1P over time, it may indicate an increase in the severity of the condition in the patient. Conversely, if there is a normalization of the concentration of S1P, it may indicate an improvement in the condition of the patient.

The methods disclosed herein are simple, marginally invasive, and require only a specimen such as blood or urine from the patient. Thus, such methods are also useful for screening patients who have not been previously diagnosed as carrying cancer, particularly patients who are at risk for cancers, especially ovarian cancer or breast cancer. Such patients include women at elevated risk by virtue of a family history of the disease, premenopausal women with anovulatory cycles, and postmenopausal women.

In addition to the detection of levels of S1P, to improve the sensitivity and/or the specificity of detection of disease, the methods of the invention may include detection of levels of other compounds, such as other sphingolipids including sphingomyelin, sphinganine, sphingosine, glycosphingolipids and ceramide, which are detectable, e.g., by mass spectroscopy (Veldhoven, et al., *FEBS Letters,* 350: 91–95 (1994)). Alternatively, or in addition, the level of lysophospholipids including the concentration of total lysophospholipid in a sample, and/or the concentration of specific types of lysophospholipids including lysophosphatidic acid (LPA), lysophosphatidyl choline (LPC), lysophosphatidyl serine (LPS), lysophosphatidyl ethanolamine (LPE), lysophosphatidyl inositol (LPI) and lysophosphatidyl glycerol (LPG) and/or the levels of glycerol-3-phosphate and its phosphatidyl derivatives may also be measured according the methods described in PCT/US99/24969 or PCT/US98/05738, which are specifically incorporated herein.

Alternatively, or in addition, proteinaceous cancer markers may be detected in conjunction with S1P in a patient. Such markers include, but not are limited to, CA125 (detectable by the method of Taylor, supra), Tac (detectable by antibody as per U.S. Pat. No. 4,545,985), soluble IL2 receptor alpha (detectable by antibody as per U.S. Pat. No. 5,351,772), mCSF(detectable by antibody as per Saitoh, et al., *J. Am. Coll. Cardiology,* 35(3):655–65 (March 2000)), OVX1 (detectable by antibody as per Martell, et al., *Intl. J. Biol. Markers,* 13(3):145–9 (1998), CEA (detectable by antibody as per Wichmann, et al., *Lanienbecks Arch. Surgery,* 385(4):271–5 (July 2000)), PSA (detectable by antibody as per Koch, et al., *J. Urology,* 164:749–53 (September 2000)), CA15-3 (detectable by antibody as per Dimas, et al., *Euro. J. Gynaecology & Oncology,* 21(3):278–81 (2000)), CA19.9 (detectable by antibody as per Kamoshida, et al., *Modern Pathology,* 13(7):736–41 (July 2000), and PLA2 (detectable by immunoassay as per U.S. Pat. No. 5,747,264).

The measurements of additional sphingolipids and/or lysophospholipids and/or proteinaceous cancer markers may be used in combination with the level of S1P detected to refine the detection of disease. As many of these compounds may be measured in a bodily fluid sample from a patient, especially plasma or serum, measurement of these markers may be easily carried out with a portion of the bodily fluid sample taken from the patient concurrently with the determination of S1P. These additional measurements may reduce the false positives and negatives associated with detection of disease in a patient using the methods of the invention. Measurements of different markers can be taken either simultaneously or sequentially from a single sample from a patient. Particularly useful measurements for increasing sensitivity are measurements of concentrations of S1P and other markers taken over time or in units of rate of change of the marker over time, to decrease false positive results.

The information on levels of S1P in samples from a patient made available by the methods of the invention may suggest additional procedures be instituted to improve the early detection of diseases such as cancer, such as ultrasound, biopsy, laparascopy, surgery, mammography, biopsy or MRI.

The following examples are presented to demonstrate the methods of the present invention and to assist one of ordinary skill in using the same. The examples are not intended in any way to otherwise limit the scope of the disclosure or the protection granted by Letters Patent granted hereon.

EXAMPLE I

Detection and Quantitation of S1P Levels in Human Plasma or Serum

Reagents

S1P lyase is prepared as described by Zhou and Saba, *Biochem. And Biophys. Res. Commun.* 242:502–507

(1998)), incorporated by reference herein. NADH:FMN oxidoreductase from *Photobacterium fischeri* and NADH are obtained from Boehringer Manheim, (Indianapolis, Ill.). Bacterial luciferase from *V. Harveyi*, is purchased from Sigma Chemical Co., St. Louis, Mo. All lipid standards including S1P, fatty acids and methyl esters are purchased from Avanti Polar Lipids, (Alabaster, Ala.) or Sigma Chemical Co. 3,5 Dichloro-2-hydroxybenzenesulfonic acid sodium salt (HDCBS) is purchased from Biosynth AG, Naperville, Ill.

Sample Collection

Whole blood specimens are collected in a serum or plasma (e.g. containing EDTA) vacutainer tube. The whole blood specimen is then centrifuged under standard conditions to provide a pellet of the blood cells and platelets and a supernatant. The serum or plasma supernatant is either processed immediately or stored at −70° C.

Sample Preparation for the Enzymatic Assay

Samples undergo organic extraction prior to enzymatic detection. Specific extraction conditions can be optimized for extraction of S1P from various samples by one skilled in the art. For example, approximately 0.1 ml of plasma or serum is added to 0.75 ml of chloroform:methanol (1:2), vortexed and centrifuged at 14,000 rpm for 5 minutes. The supernatant is decanted into a new tube to which is added 0.25 ml of chloroform and 0.35 ml of water. This mixture is vortexed and centrifuged as above to yield a biphasic solution. The lower layer is discarded and to the remaining upper layer is added 0.5 ml chloroform. The sample is vortexed and centrifuged again at 14,000 rpm for 5 minutes. Once again the lower layer is discarded. To the upper layer, 0.5 ml chloroform and 12.6 $\mu$l concentrated hydrochloric acid are added, the mixture is vortexed and centrifuged as before. The acidified lower layer is collected and transferred to a clean tube. The sample is evaporated completely under nitrogen and reconstituted in 100 $\mu$l of sample buffer containing 2.5% Triton X-100, 10 mM EDTA and 100 mM potassium phosphate (pH 7.4). The sample is stored at −70° C. until assayed.

Enzyme Assay

In the first of two matched wells of a 96 well microtiter plate, 5–100 $\mu$l of the extracted lipid plasma or serum sample is incubated with 0.25 units of S1P Lyase in 100 mM potassium phosphate, 10 mM EDTA, 1 mM pyroxidal phosphate (pH 7.4) at 37° C. for 30–60 minutes to produce ethanolamine-phosphate and long-chain aldehyde (e.g. hexadecanal) from S1P. In the second well of each set an identical amount of sample and reaction buffer without lyase is aliquotted and subjected to the same incubation conditions.

The presence of long-chain aldehyde (e.g. hexadecanal) is detected using a luminescent reaction that utilizes bacterial luciferase and NAD(P)H:FMN oxidoreductase. NADH is added to each well to a final concentration of 13 mM. The plate is read for background. 100 $\mu$l of enzyme mixture containing 0.8 mg bacterial luciferase and 0.2 U NADH-:FMN is added to each reaction well. The reaction is incubated for five (5) minutes at room temperature and then read using a luminometer (Wallac Victor2 Multilabel Counter, EG&G Wallac Inc., Gaithersburg, Md.).

Numerical values for concentrations of S1P are obtained from a standard curve constructed from known S1P amounts. Alternatively, a standard curve may be generated from known amounts of long-chain aldehyde (e.g. hexadecanal). An internal standard of extracted plasma is included within each assay (i.e. each plate) that is measured at different dilutions. In some cases, this internal standard is used to correct for variations between different experiments. Internal standards are also measured in the absence of S1P lyase enzyme (i.e., the second of the matched pairs of wells). This "no-enzyme" sample provides a background value that is subtracted from each unknown when calculating the S1P levels using the long-chain aldehyde (e.g. hexadecanal) measurement.

EXAMPLE II

Detection and Quantification of S1P in Samples from Patients Having Cancer

S1P levels are determined in a sample, such as serum or plasma, from a patient. For example, blood may be collected from patients and is processed as described above in Example I. Plasma from the samples is prepared for the enzymatic assay of the invention as described above in Example I. To diagnose or screen patients for cancer, the data obtained from the S1P measurement is compared to a control or "normal" value that typically represents a cut-off level for additional testing or clinical diagnosis. In practice, the S1P data is correlated to the disease state by using a predetermined set of values that are particular for the assay that is employed. Moreover, the specific source of the patient sample e.g. blood or plasma, may dictate a distinct correlation step. Typically, the enzyme assay is performed as described above in Example I. The S1P levels obtained from patients having cancer exhibit a marked, significant aberration in S1P levels as compared with the levels of S1P in the plasma of non-cancer patients.

The methods described above for measuring S1P concentration in a patient sample may also be performed by using a pre-assembled diagnostic kit. Diagnostic kits typically contain reagents for measuring the concentration of S1P, and other reagents for processing the patient sample. In the embodiments described above, the kit would contain the enzymatic reagents required for measuring S1P, and may contain correlation values allowing the user to match the data obtained from the S1P measurement with normal or control data providing at cut-off value at which further clinical diagnosis is performed.

Various publications are cited herein which are hereby incorporated by reference in their entirety.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

What is claimed is:

1. A non-radiographic method for cancer detection comprising:
   (1) extracting sphingolipids from a patient sample to yield a sphingolipid enriched mixture;
   (2) subjecting at least a portion of the mixture to an enzymatic reaction to produce a non-radiographic signal;
   (3) determining the concentration of S1P present in the sample by measuring the signal, and
   (4) comparing the concentration to a normal or control value to indicate the presence or absence of cancer in the patient.

2. The method of claim wherein the bodily fluid is plasma or serum.

3. The method of claim 1 wherein the enzymatic reaction uses S1P lyase.

4. The method of claim 1 wherein the enzymatic reaction uses a substrate selected from the group consisting of S1P, a long-chain aldehyde, and ethanolamine-1-phosphate.

5. The method of claim 1 further comprising establishing a background level of S1P.

6. The method of claim 5 further comprising the step of subtracting the background level from the concentration of S1P in the patient sample.

7. The method of claim 1, wherein the extracting step uses organic solvents.

8. The method of claim 1 wherein the non-radiographic signal is selected from the group consisting of light, a fluorescent product, and a spectrophotometrically detectable product.

9. The method of claim 1 wherein the enzymatic reaction is luminescent.

10. The method of claim 9 wherein the enzymatic reaction uses a bacterial luciferase.

11. The method of claim 10 wherein NAD(P)H:FMN oxidoreductase recycles FMN produced by the bacterial luciferase.

12. The method of claim 1 wherein NAD(P)H dependent aldehyde dehydrogenase produces the non-radiographic signal.

13. The method of claim 1 wherein NADH dependent aldehyde dehydrogenase and an NAD(P)H dependent aldehyde dehydrogenase produces the non-radiographic signal.

14. The method of claim 13 wherein the signal is produced by accumulation of NADH or oxidation of NAD(P)H.

15. A method for cancer detection in a patient comprising:
   (1) collecting a sample of patient bodily fluid;
   (2) assaying for the concentration of S1P in the sample by mass spectrometry; and
   (3) correlating the concentration of S1P in the sample with cancer in the patient.

16. The method of claim 15 wherein the sample is enriched for S1P between the collecting step and the assaying step.

17. The method of claim 15 wherein the assaying step is further comprised of liquid or gas chromatography.

18. The method of claim 15 wherein the cancer is selected from the group consisting of cervical, uterine, endometrial, peritoneal, and fallopian tube cancer.

19. The method of claim 15 wherein the cancer is ovarian cancer.

20. The method of claim 15 wherein the cancer is breast cancer.

21. The method of claim 15 wherein the sample is a plasma specimen.

22. The method of claim 15 wherein the sample is a serum specimen.

23. The method of claim 15 wherein the step of correlating the concentration of S1P with cancer includes comparison with a normal or control value.

24. The method of claim 15 wherein the step of correlating the concentration of S1P with cancer includes comparison with a threshold value.

25. The method of claim 15 wherein the assaying step is carried out in an automated assay system.

26. The method of claim 15 further comprising the step of determining the concentration in the sample of at least one of total lysophospholipid, LPA, LPC, LPS, LPE, LPI, LPG, glycerol-3-phosphate, GPC, CRS, GPE, GPI, GPG, sphingomyelin, sphinganine, sphingosine, glycosphingolipids, ceramide, CA125, Tac, soluble IL2 receptor α, mCSF, OVX1, CEA, PSA, CA15-3, CA19.9, or PLA2.

27. The method of claim 1 further comprising the step of determining the concentration in the sample of at least one of total lysophospholipid, LPA, LPC, LPS, LPE, LPI, LPG, glycerol-3-phosphate, GPC, CRS, GPE, GPI, GPG, sphingomyelin, sphinganine, sphingosine, glycosphingolipids, ceramide, CA125, Tac, soluble IL2 receptor α, mCSF, OVXI, CEA, PSA, CA15-3, CA19.9, or PLA2.

* * * * *